(12) United States Patent
Ashida et al.

(10) Patent No.: US 8,382,659 B2
(45) Date of Patent: Feb. 26, 2013

(54) ENDOSCOPE APPARATUS AND CONTROLLING METHOD THEREOF COMPRISING CURVING CONTROL MECHANISM

(75) Inventors: Tsuyoshi Ashida, Kanagawa (JP); Hiroyuki Hasegawa, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 310 days.

(21) Appl. No.: 12/834,395

(22) Filed: Jul. 12, 2010

(65) Prior Publication Data

US 2011/0009698 A1 Jan. 13, 2011

(30) Foreign Application Priority Data

Jul. 13, 2009 (JP) ................ P2009-164692

(51) Int. Cl.
*A61B 1/005* (2006.01)
(52) U.S. Cl. .............. 600/146; 600/145; 600/152
(58) Field of Classification Search .............. 600/145, 600/146, 152, 118
See application file for complete search history.

(56) References Cited

U.S. PATENT DOCUMENTS

| | | | | |
|---|---|---|---|---|
| 6,866,671 B2* | 3/2005 | Tierney et al. | ................. | 606/130 |
| 7,828,723 B2* | 11/2010 | Ueno et al. | ................... | 600/136 |
| 2003/0092965 A1* | 5/2003 | Konomura et al. | ........... | 600/146 |
| 2004/0049097 A1* | 3/2004 | Miyake | ........................ | 600/150 |
| 2004/0193016 A1* | 9/2004 | Root et al. | ..................... | 600/146 |
| 2008/0262306 A1* | 10/2008 | Kawai | ............................. | 600/118 |
| 2009/0076330 A1* | 3/2009 | Ashida | ........................ | 600/146 |
| 2009/0227841 A1* | 9/2009 | Miyako et al. | ................ | 600/139 |
| 2009/0259099 A1* | 10/2009 | Zhou et al. | .................... | 600/109 |
| 2010/0210908 A1* | 8/2010 | Ashida et al. | ................. | 600/145 |
| 2011/0065994 A1* | 3/2011 | Kudoh et al. | ................. | 600/146 |

FOREIGN PATENT DOCUMENTS

JP 2009-90087 A 4/2009

* cited by examiner

*Primary Examiner* — John P Leubecker
(74) *Attorney, Agent, or Firm* — Birch, Stewart, Kolasch & Birch, LLP

(57) ABSTRACT

An endoscope apparatus includes an endoscope main body and an assisting drive unit. The endoscope main body includes an endoscope insertion portion having a curving portion on the leading end side thereof, a curving operation portion operating or curving the curving portion, and a curving drive portion driving or curving the curving portion according to an operation force applied to the curving operation portion. The assisting drive unit generates a drive force assisting a curving drive operation to be carried out by the curving drive portion. Curving information regulated at each curving angle corresponding to curving amount of the curving portion is stored previously. The curving amount $\theta a$ of the curving portion is detected. The drive force is generated from the assisting drive unit using the curving information corresponding to the detected curving amount $\theta a$.

15 Claims, 11 Drawing Sheets

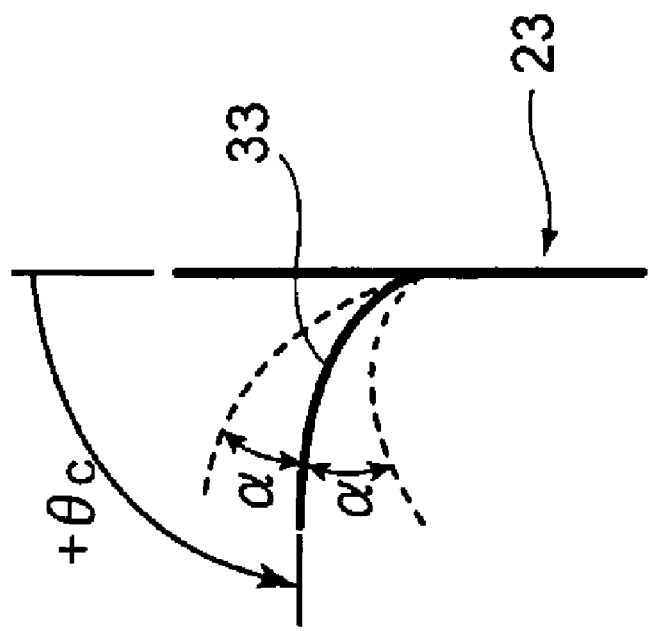
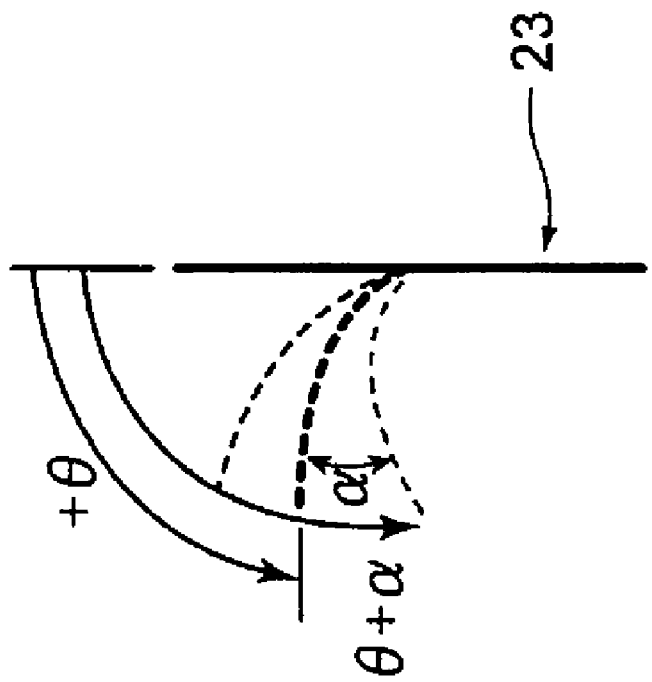

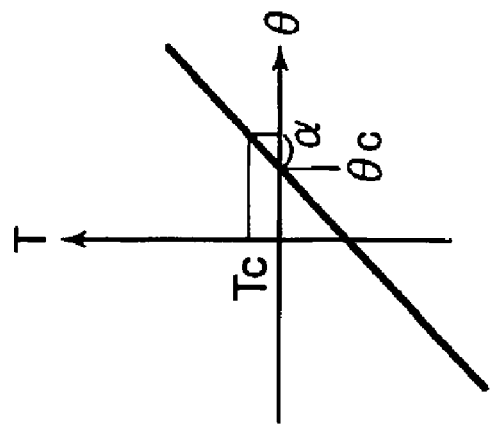
FIG. 7A — LOAD OF ENDOSCOPE ITSELF
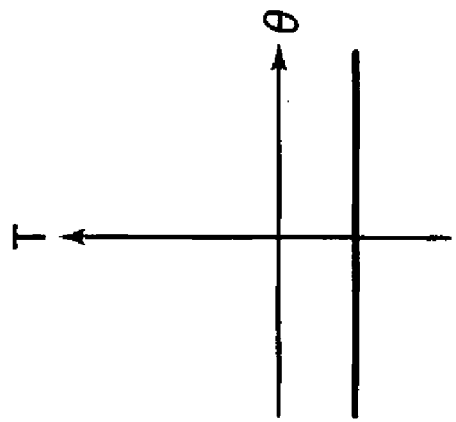
FIG. 7B — TORQUE OF DRIVE MOTOR FOR RE-SETTING NEUTRAL POINT
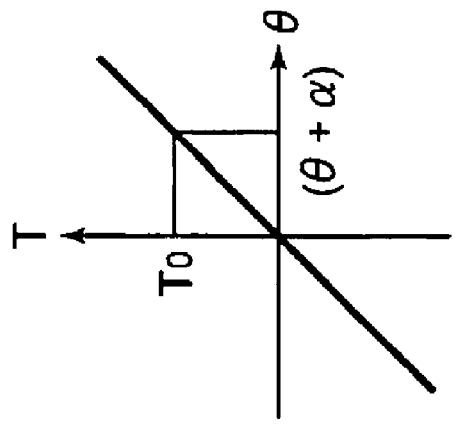
FIG. 7C — TOTAL LOAD

ENDOSCOPE APPARATUS AND CONTROLLING METHOD THEREOF COMPRISING CURVING CONTROL MECHANISM

CROSS-REFERENCE TO RELATED APPLICATIONS

This application claims the benefit of Japanese Patent Application No.2009-164692, filed on Jul. 13, 2009, the entire contents of which are hereby incorporated by reference, the same as if set forth at length; the entire of which are incorporated herein by reference.

BACKGROUND OF THE INVENTION

1. Technical Field

The present invention relates to an endoscope apparatus, an endoscope system and a method for controlling an endoscope apparatus.

2. Description of Related Art

As an apparatus for observing the inside of a body cavity, the inside of a tube included in a structure, and the like, there is widely used an endoscope apparatus. The endoscope apparatus includes an endoscope insertion portion to be inserted into a sample, and a main body operation portion disposed continuously with the base end of the endoscope insertion portion, while on the leading end side of the endoscope insertion portion, there is formed a curving portion which can be curved through the pulling operation of an operation wire inserted through the endoscope insertion portion. The operation wire can be pulled by operating an angle knob disposed on the main body operation portion in a desired direction to thereby curve the curving portion in a desired direction. As an example of such endoscope apparatus, there is disclosed in JP-A-2009-90087 an endoscope apparatus with a power assisting function structured such that, in order to reduce the operation force of the angle knob for curving the curing portion, an operation assisting force for assisting the pulling of the operation wire is generated using an assisting drive motor to thereby apply the operation assisting force to a wire pulling member. According to the disclosed endoscope apparatus, in addition to the operation force of the angle knob to be applied by an operator who operates the endoscope apparatus, the operation assisting force generated by the drive motor provided within the main body operation portion is applied to the angle knob. Therefore, while reducing the operation force, the curving portion can be curved by a desired amount.

In the case of the above-mentioned operation assisting force, while the size of the operation assisting force is set according to the operation of the angle knob, the operation assisting force is applied as the operation assisting force of the operator. However, the desired characteristics of the operation force to be applied to the curving operation portion vary depending on the taste of the operator, the manipulation contents of diagnose and care using the endoscope apparatus, or on the individual difference between endoscopes such as the bending rigidity of the respective endoscope insertion portions thereof. Therefore, it is expected that the curving characteristic itself expressing the relationship between the operation force to be applied to the angle knob and the curving angle of the curving portion can be changed, whereby the feeling of the operator in using the endoscope can be made more natural.

SUMMARY

It is an object of the present invention to provide an endoscope apparatus and an endoscope system which are capable of matching the relationship between the operation force for curving the curving portion and the actual curving amount to an arbitrary characteristic, and a method for controlling such endoscope apparatus.

The present invention is described by the following articles.

(1) An endoscope apparatus includes an endoscope main body, a curving amount detecting unit, an assisting drive unit, a storage unit and a control unit. The endoscope main body includes (i) an endoscope insertion portion having a curving portion on the leading end side thereof, (ii) a curving operation portion operating or curving the curving portion, and (iii) a curving drive portion driving or curving the curving portion according to an operation force applied to the curving operation portion. The curving amount detecting unit detects curving amount of the curving portion. The assisting drive unit generates a drive force for assisting a curving drive operation carried out by the curving drive portion. The storage unit stores multiple pieces of curving information respectively regulated at every curving angles corresponding to curving amounts of the curving portion. The control unit controls the assisting drive unit to generate the drive force according to the curving amount detected by the curving amount detecting unit. The control unit controls the assisting drive unit to generate the drive force using the curving information stored in the storage unit.

(2) An endoscope system includes an endoscope apparatus according to (1) and an external electronic equipment. The external electronic equipment is connected to the endoscope apparatus in such a manner that it is allowed to communicate with the endoscope apparatus. The storage unit stores the curving information in a storage portion provided in the external electronic equipment.

(3) A method for controlling an endoscope apparatus which includes an endoscope main body and an assisting drive. The endoscope main body includes (i) an endoscope insertion portion having a curving portion on the leading end side thereof, (ii) a curving operation portion operating or curving the curving portion and (iii) a curving drive portion driving or curving the curving portion according to an operation force to be applied to the curving operation portion. The assisting drive unit generates a drive force for assisting a curving drive operation to be carried out by the curving drive portion. The endoscope controlling method includes: storing curving information regulated at each curving angle corresponding to curving amounts of the curving portion previously; detecting curving amount of the curving portion; and generating the drive force by the assisting drive unit using the curving information corresponding to the detected curving amount.

With use of an endoscope apparatus, an endoscope system and a method for controlling such endoscope apparatus according to the invention, the relationship between the operation force for curving the curving portion and the actual curving amount can be matched to an arbitrary characteristic. Owing to this, regardless of the types of endoscope apparatuses and individual difference between them, the curing operation can be executed with the same operation force and also there can be obtained a good operation characteristic which is fit to the manipulation of diagnosis and care and the taste of the operator.

BRIEF DESCRIPTION OF THE DRAWINGS

FIG. 6 is a graphical representation of a neutral point of the curving portion. Specifically, FIG. 6A is an explanatory view of a neutral point in the case that the curving portion is held in a straight state, and FIG. 6B is an explanatory view of a neutral point in the case that the curving portion is curved by an angle of θc.

FIG. 7 is a graphical representation of the relationship between a curving angle and a torque necessary for curving the curving portion. Specifically, FIG. 7A is an explanatory view of a torque characteristic in the straight state of the curving portion, FIG. 7B is an explanatory view of the torque characteristic of a drive motor for re-setting a neutral point, and FIG. 7C is an explanatory view of the torque characteristic in the case that the neutral point is re-set.

FIG. 11 is an operation explanatory view of the curving operation. Specifically.

DETAILED DESCRIPTION OF EMBODIMENTS OF THE INVENTION

Figure 1:
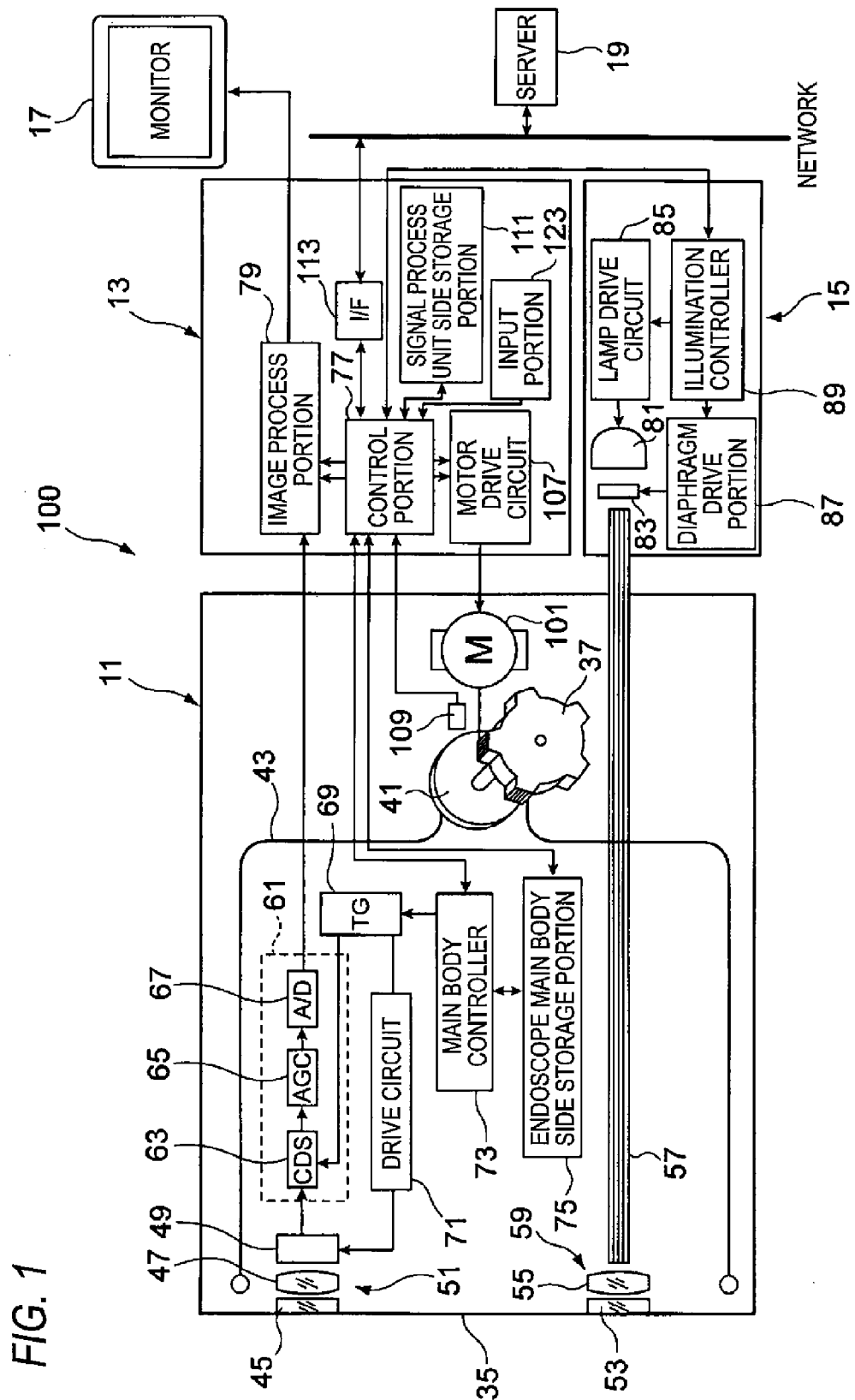
FIG. 1 is a view to explain an embodiment according to the invention and is a typical block diagram of an endoscope system according to the invention.

Firstly, description will be given of the basic structure of an endoscope system. FIG. 1 is an explanatory view of an embodiment according to the invention and is a typical block diagram of the structure of the present endoscope system.

This endoscope system 100 includes an endoscope main body 11, a signal process unit 13 for signal processing image information which is output from the endoscope main body 11, and a light source unit 15 for supplying an illumination light to the endoscope main body 11. To the signal process unit 13, there is connected a monitor 17 which is used to display the image information after an image is processed. Also, an endoscope apparatus, which includes the endoscope main body 11, signal process unit 13 and light source unit 15, can be connected through a network to external equipment such as a server 19 as the need arises. Here, to the network, there are connected various pieces of network connecting equipment (not shown) such as a storage device, whereby various kinds of information can be shared in common.

Figure 2:
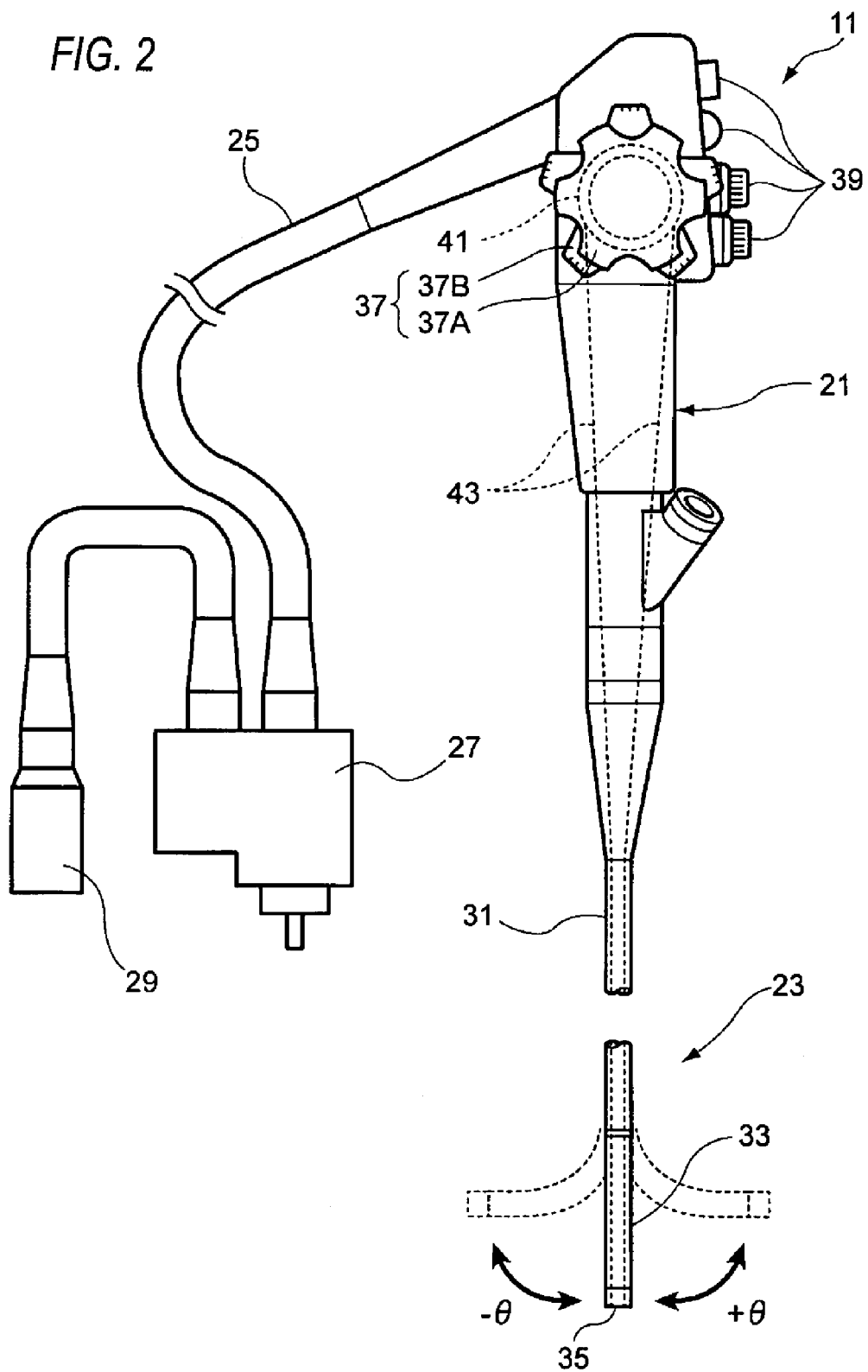
FIG. 2 is a schematic outside view of an endoscope apparatus shown in FIG. 1.

The endoscope main body 11, as the schematic outside view thereof is shown in FIG. 2, includes a main body operation portion 21 and an endoscope insertion portion 23 which is arranged continuously with the main body operation portion 21 and can be inserted into a subject. Also, to the operation portion 21, there is connected a universal cord 25 and, on the leading end of the universal cord 25, there is provided a light guide connector 27. The light guide connector 27 is removably connected to the light source unit 15 shown in FIG. 1, whereby an illumination light can be transmitted to an illumination optical system provided within the endoscope insertion portion 23. Also, to the light guide connector 27, there is connected a video connector 29, while the video connector 29 can be removably connected to the signal process unit 13 shown in FIG. 1.

The endoscope insertion portion 23, which is covered with resin material, includes a soft portion 31, a curving portion 33 and a leading end portion (which is also referred to as an endoscope leading end portion) 35 in this order sequentially from the side of the main body operation portion 21. The curving portion 33 can be operated or curved remotely by rotating the curving operation portion 37 (angle knobs 37A, 37B) of the main body operation portion 21. Specifically, on the rotation shaft of the angle knobs 37A and 37B, there is provided a pulley 41 coaxially therewith; and, between the pulley 41 and endoscope leading end portion 35, there is interposed an operation wire 43 wound around the pulley 41 in such a manner that it extends along the inner wall of the endoscope leading end portion 35. The two ends of the operation wire 43 are fixed to the endoscope leading end portion 35. Owing to this structure, by rotationally operating the angle knobs 37A and 37B respectively, the operation wire 43 can be pulled to curve the curing portion 33, whereby the endoscope leading end portion 35 can be directed in a desired direction.

Here, in the illustrated example, there is shown one system which curves the curving portion in the ± direction in correspondence to the angle knob 37A. However, actually, in the main body operation portion 21 and endoscope insertion portion 23, there is also incorporated another system which curves the curving portion in a direction perpendicular to the above direction (the vertical direction of the sheet of FIG. 2: which is referred to as a vertical direction) in correspondence to the angle knob 37B. That is, by operating the angle knobs 37A and 37B, the endoscope leading end portion 35 can be curved freely in the right and left direction and also in the vertical direction perpendicular thereto.

Also, on the main body operation portion 21, in addition to the above-mentioned angle knobs 37A and 37B, there are also provided various buttons 39 such as an air feed/water feed button, a suction button and a shutter button. Thus, an operator, while operating these buttons, observes or treats the observation area of the subject existing in front of the endoscope leading end portion 35.

Referring back again to FIG. 1, description will be given of the structure of the endoscope main body 11.

On the endoscope leading end portion 35 of the endoscope main body 11, there is disposed an imaging optical system 51 which includes an observation window 45, an image forming lens 47, and an imaging device 49 such as an image sensor of a CCD (Charge Coupled Device) type or a CMOS (Complementary Metal Oxide Semiconductor) type. Also, on the endoscope leading end portion 35, there is also disposed an illumination optical system 59 which includes an illumination window 53, a diffusion lens 55 and a bundle of optical fibers.

Here, an output signal from the imaging device 49 is taken into an analog front end (AFE) circuit 61. The AFE circuit 61 includes a correlation dual sampling (CDS) circuit 63, an auto gain control (AGC) circuit 65, and an analog/digital (A/D)

converter 67. And, the AFE circuit 61, when receiving a trigger signal transmitted from a timing generator (TG) 69, converts the output signal from the imaging device 49 to a digital image signal and then outputs such digital image signal. Also, to the imaging device 49, there is applied from a drive circuit 71 a drive signal which is generated according to the trigger signal from the TG 69.

The imaging process to be carried out by the above-mentioned imaging optical system 51 is controlled by a main body controller 73. The main body controller 73 is connected to the control portion 77 of the signal process unit 13 through the universal cord 25 and video connector 29 (see FIG. 2) both of which have been discussed above in such a manner that it is allowed to communicate with the control portion 77. Also, in the endoscope main body 11, there is included an endoscope main body side storage portion 75 which is connected to the control portion 77 and also in which various pieces of information can be stored.

Also, the control portion 77 is connected to an image process portion 79 which is used to process a picked-up image. The image process portion 79 is connected to the output side of the AFE circuit 61 and, on receiving an instruction from the control portion 77, displays on the monitor 17 information about the picked-up image that has been image processed, whereby an endoscope diagnosis using an observed image can be realized.

And, one end side of the light guide 57 is connected to the illumination optical system 59, while the other end side thereof is connected to the light source unit 15 through the universal cord 25 and light guide connector 27 (see FIG. 2). The thus structured light guide 57 introduces therein the light from a lamp 81 using a xenon bulb or the like through an optical diaphragm device 83. The lamp 81 can be controlled or driven by a lamp drive circuit 85, while the optical diaphragm device 83 can be controlled by a diaphragm drive portion 87. And, the lamp drive circuit 85 and diaphragm drive portion 87 can be controlled by an illumination controller 89 which is connected to the control portion 77 of the signal process unit 13.

Figure 3:
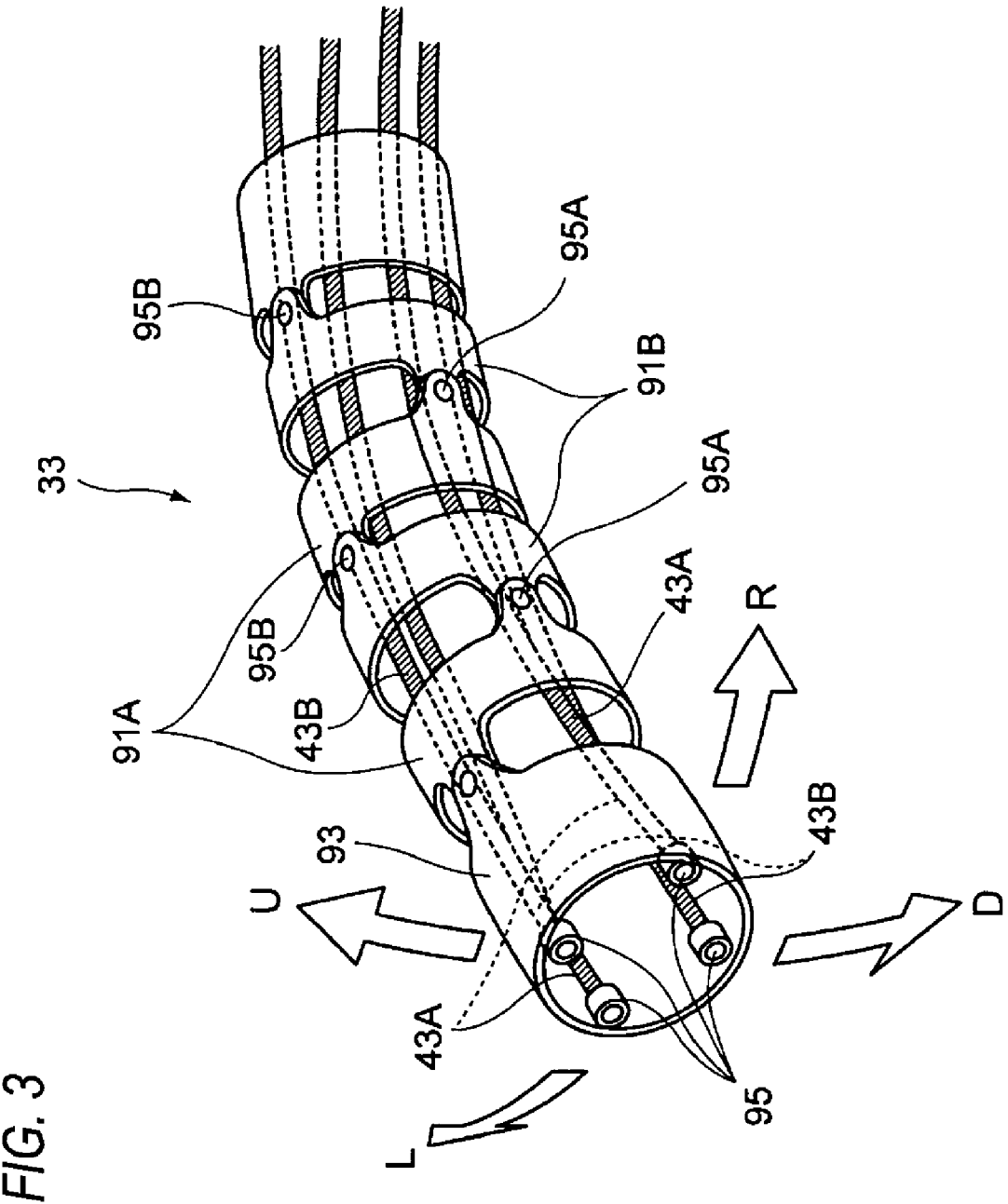
FIG. 3 is a schematic structure view of the curving mechanism of a curving portion included in the endoscope apparatus.

FIG. 3 shows the curving mechanism of the curving portion schematically.

The curving portion 33 can be curved in the right and left direction and in the vertical direction perpendicular thereto by rotationally operating the angle knobs 37A and 37B. Like the illustrated example, the curving portion 33, similarly to the curving portion of a known endoscope, has a structure in which a large number of circular node rings 91A, 91B are arranged alternately. On the inner wall surfaces of the respective node rings 91A, 91B constituting the curving portion 33, there are arranged operation wires 43A respectively for curving the curving portion 33 in the L, R directions, and operation wires 43B respectively for curving the curving portion 33 in the U, D directions. The end portions of the operation wires 43A and 43B are respectively fixed to fixing portions 95 respectively formed in a sleeve 93 which exists on the leading end side of the endoscope.

The operation wires 43A are arranged side by side along the longitudinal direction of the curving portion 33, while one end portion of each operation wire 43A on the sleeve 93 side and the other end portion thereof are disposed as a pair at positions spaced from each other in the diameter direction of the curving portion 33. Also, the operation wires 43B, similarly to the operation wires 43A, are disposed as a pair in the peripheral positions shifted in phase by 90 degrees from the operation wires 43A.

The node rings 91A and 91B are connected to each other by two connecting pins 95A and 95B which are disposed as a pair in the diameter direction of the rings, while the pair of connecting pins 95A and the pair of connecting pins 95B are disposed at the peripheral positions of the rings in such a manner that they are shifted in phase 90 degrees from each other. That is, the node rings 91A, 91B are rotatably connected to each other alternately in the L, R directions and U, D directions.

The endoscope system 100 having the above basic structure has a power assisting function to generate an operation assisting force in order that the endoscope system 100 can operate the angle knobs 37A, 37B with excellent operation efficiency when curving the curving portion 33, that is, the relationship between the operation forces to be applied to the angle knobs 37A, 37B and the curving angle of the curving portion 33 can provide a desired relationship between them. Now, description will be given below of this power assisting function.

Firstly, description will be given of an example of the drive mechanism that generates the above operation assisting force.

Figure 4:
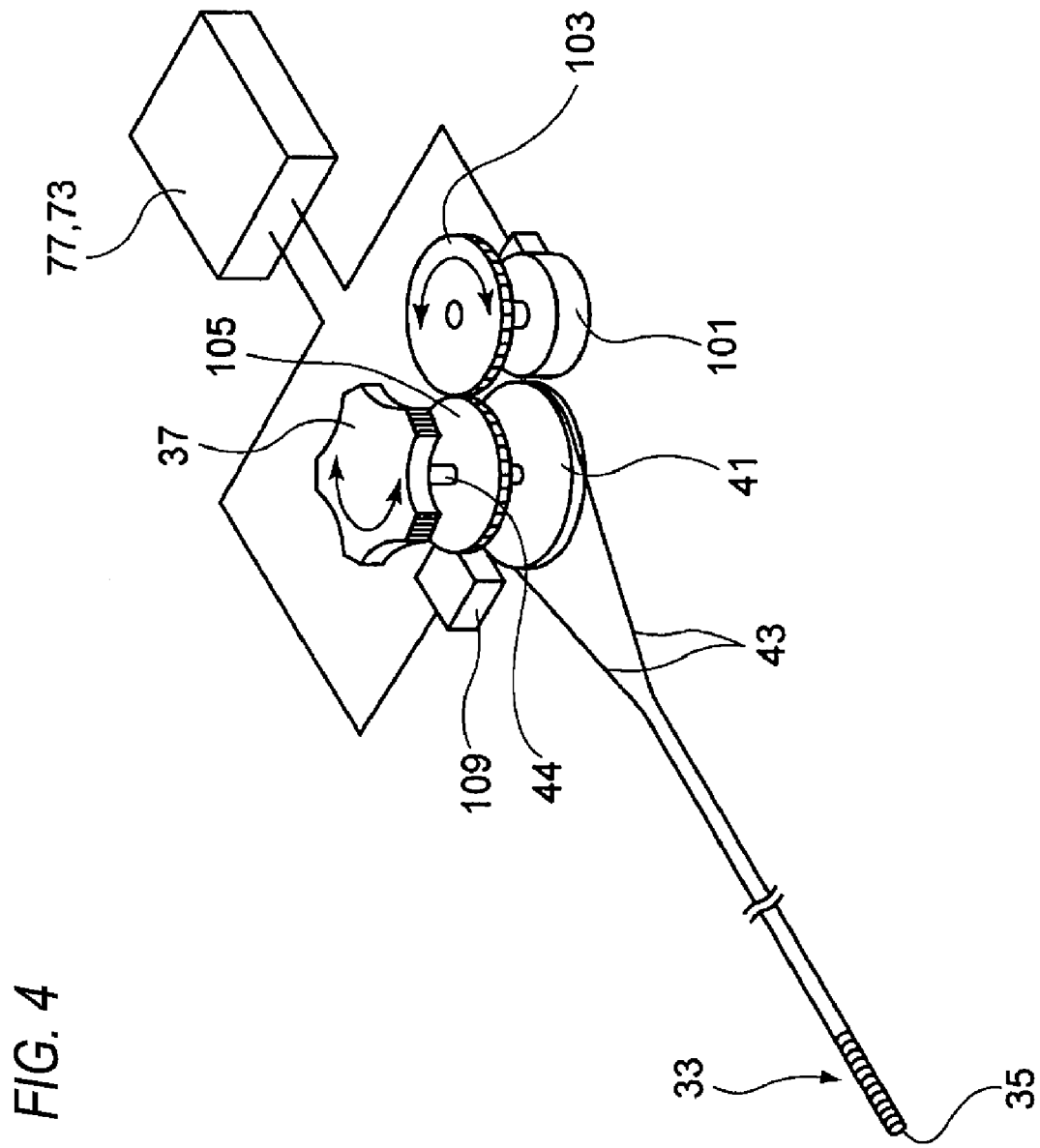
FIG. 4 is a schematic typical structure view of a drive mechanism for curving the curving portion.

FIG. 4 is a typical structure view of a curving drive portion which is used to curve the curving portion. The curving drive portion includes a curving operation portion 37 which carries out a manual operation for curving the curving portion 33, an operation wire 43 for transmitting an operation force from the curving operation portion 37 to the curving portion 33, and a pulley 41 which is disposed coaxially with the curving operation portion 37 and on which the operation wire 43 is wound. The curving operation portion 37 and pulley 41 for paying out the operation wire 43 therefrom are rotatably supported around a connecting shaft 44, while a rotation operation force to be applied to the curving operation portion 37 is transmitted directly to the pulley 41 through the connecting shaft 44. Therefore, in the case that the curving operation portion 37 is manually operated or rotated, the pulley 41 is rotated according to the manual operation, and thus the draw-in and pay-out operations of the operation wire 43 are carried out, whereby the curving portion 33 is curved by the above-mentioned curving mechanism (see FIG. 3).

Also, this curving drive portion includes a drive motor 101 which is used to apply an operation assisting torque to the connecting shaft 44. The drive motor 101 functions as an assisting drive device which supplies a rotation drive force to the connecting shaft 44 through a drive gear 103 and a driven gear 105. To the drive motor 101, from a motor drive circuit 107 (see FIG. 1) connected to the control portion 77, there is applied a motor drive electric power which is necessary to generate the operation assisting torque. Here, although the drive motor 101 is structured such that it can drive the connecting shaft 44 through the drive gear 103 and driven gear 105, the structure of the drive motor 101 may also be changed properly; for example, the drive motor 101 may also be structured such that it drives the connecting shaft 44 directly.

Further, the curving drive portion includes an encoder 109 which is used to detect the amount of rotation of the connecting shaft 44 and outputs to the control portion 77 signals expressing the detected amounts of rotation of the connecting shaft 44 sequentially. In the illustrated example, the encoder 109 detects the amounts of rotation of the connecting shaft 44 according to the displacement of the circumferential portion of the pulley 41. The control portion 77, according to the signals expressing the amounts of rotation of the connecting shafts 44 output from the encoder 109, obtains the drawing-in amounts of the operation wire 43 using various conditions such as the radius distance of the pulley 41 and calculates the amount of curving (angle of curving) of the curving portion 33 due to such drawing-in amounts of the operation wire 43.

In other words, the encoder 109 functions as a detector for detecting the amounts of curving of the curving portion 33.

Here, in the case of the encoder 109, there may also be employed other structures than the above structure in which it detects the amounts of rotation of the connecting shaft 44 from the displacement of the pulley 41; for example, there may also be employed a structure in which it detects the amounts of rotation of the pulley 41 according to the amounts of displacement of other member that is operated following the curving operation portion 37. Specifically, the encoder 109 may also be structured such that it uses a sensor for detecting the amounts of movement of the operation wire 43, or it uses a potentiometer for detecting the angles of rotation of the angle knobs 37A and 37B. Also, in the case that the drive motor 101 is a motor for outputting an encode signal, the encoder 109 may also use such encode signal.

There is connected to or provided in the control portion 77 a storage portion in which curving characteristic information (the detailed of which will be discussed later) representing the relationship between the curving amount of the curving portion 33 and an operation assisting torque to be generated is stored. The control portion 77 obtains a necessary operation assisting torque according to the curving amount of the curving portion 33 and allows the drive motor 101 to generate this operation assisting torque, thereby controlling the operation to assist the curving drive of the curving portion 33. In other words, the control portion 77, according to predetermined curving characteristic information, obtains motor drive electric power for driving the drive motor 101, and allows the motor drive circuit 107 to output the motor drive electric power.

Owing to the above structure, according to the curving amount of the curving portion 33 to be generated by an operation force applied to the curving operation portion 37, an operation assisting torque corresponding to this curving amount is applied to the connecting shaft 44 through the driving of the drive motor 101 and thus the pulley 41 is rotated, thereby assisting the curving operation of the curving portion 33.

Next, description will be given below of curving characteristic information which regulates the relationship between the operation force to be applied to the curving operation portion 37 (angle knobs 37A and 37B) and the curving angle θ of the curving portion 33 in such a manner that a curving operation to be carried out by an operator can provide a desired operation feeling, that is, the curving characteristic that regulates the operation assisting force to be applied to the connecting shaft 44 for each of the curving angles.

Figure 5:
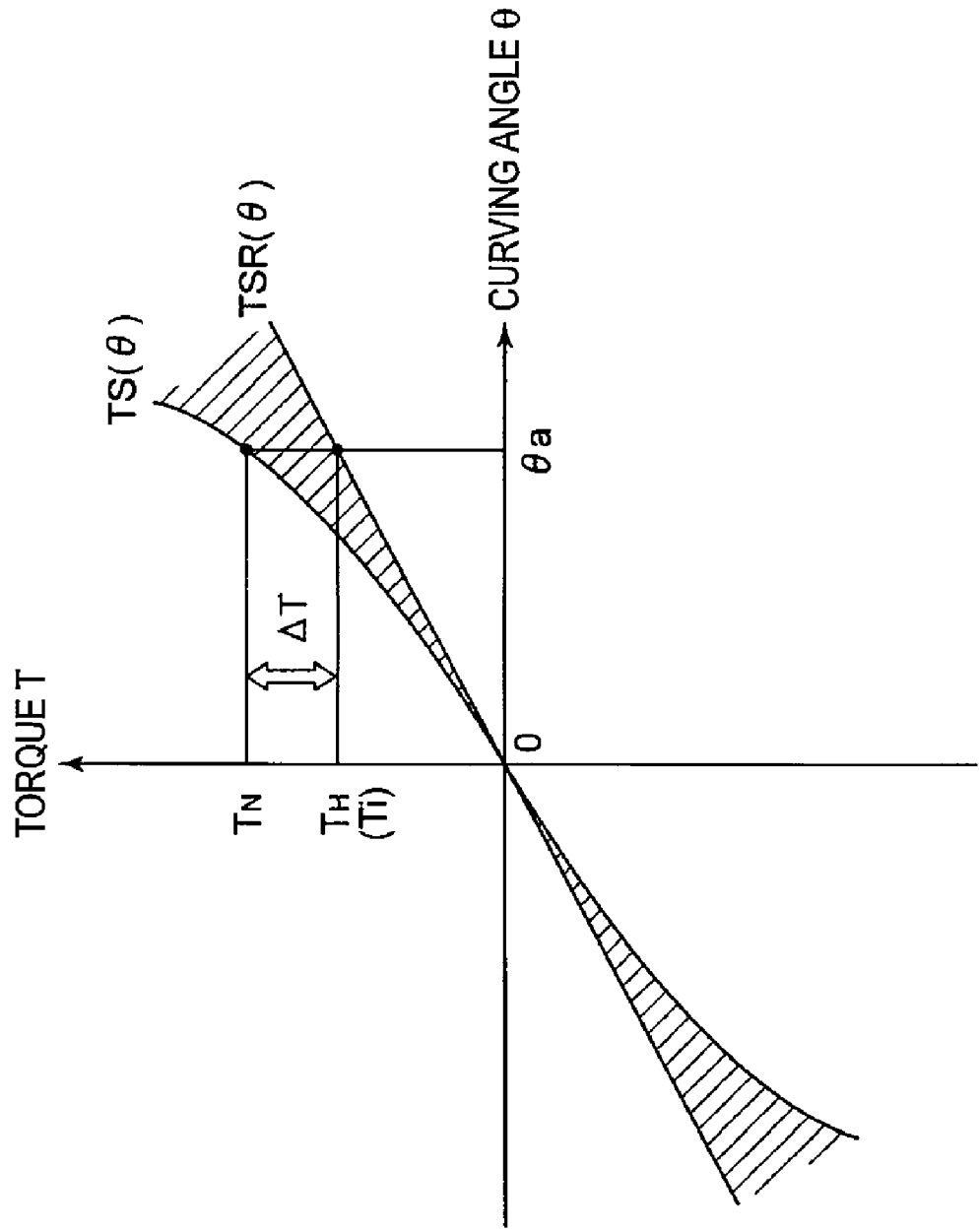
FIG. 5 is a graphical representation of a necessary torque characteristic TS (θ) necessary for the curving angle of the curving portion and an arbitrary torque characteristic TSR (θ) which can be defined arbitrarily.

FIG. 5 shows the relationship between a necessary torque characteristic TS (θ) (a first curving characteristic) with respect to the curving angle of the curving portion and an arbitrary torque characteristic TSR (θ) (a second curving characteristic) which can be defined arbitrarily.

The necessary torque characteristic TS (θ) is the characteristic that, according to the bending rigidity of the curving portion 33 to be decided depending on the material and structure of the endoscope insertion portion 23, regulates a torque value necessary to be applied to the connecting shaft 44 in order to maintain the curving portion 33 at a specific curving angle θ.

The arbitrary torque characteristic TSR (θ) is a torque characteristic which can be set arbitrarily by the operator of the endoscope apparatus and also which represents the arbitrary characteristic of the relationship between an operation torque produced in the connecting shaft 44 when operating the curving operation portion 37 and the curving angle θ of the curving portion 33 variable according to the operation torque. The control portion 77 controls the actual curving operation of the curving portion 33 in such a manner that it provides an operation based on the arbitrary torque characteristic TSR (θ).

Here, description will be given below of the contents of a torque which is applied to the connecting shaft 44 when the curving operation portion 37 is operated to thereby curve the curving portion 33 to a certain curving angle θa.

As shown in FIG. 5, a torque TN, which is necessary to curve the curving portion 33 to the curving angle θa, can be obtained from the necessary torque characteristic TS (θ). Here, the necessary torque characteristic TS (θ) has a non-linear characteristic according to which the larger the curving angle θ is, the larger the torque increase ratio is. On the other hand, the arbitrary torque characteristic TSR (θ) here regulates a linear characteristic according to which the torque increase ratio is constant over the entire area of the curving angle θ.

In the case that the curving angle of the curving portion 33 is θa, the torque TN necessary to curve the curving portion 33 can be obtained from an operation torque TH produced by an operation force to be actually applied to the curving operation portion 37 and also from a drive torque produced by an operation assisting force to be generated by the above-mentioned drive mechanism. The then operation torque TH is controlled in such a manner that it is equivalent to an arbitrary torque Ti according to the arbitrary torque characteristic TSR (θ). That is, according to an instruction given from the control portion 77, the arbitrary torque Ti according to the arbitrary torque characteristic TSR (θ) is subtracted from the necessary torque TN according to the necessary torque characteristic TS (θ) to obtain a difference torque (difference force) Δt, and the difference torque Δt is generated from the drive motor 101 as a curving assisting force, with the result that the operation torque TH becomes equal to the arbitrary torque Ti. Owing to this control, the operation assisting force is set such that it can cancel the non-linear characteristic of the necessary torque TN, whereby the operation torque TH coincides with the arbitrary torque characteristic TSR (θ).

This allows the operator of the endoscope apparatus to always carry out the curving operation according to such curving characteristic as regulated by the arbitrary torque characteristic TSR (θ) regardless of the bending rigidity of the curving portion 33 differing in the respective endoscope apparatus. Also, in the illustrated example, the operation torque to be applied to the connecting shaft 44 due to the operation of the curving operation portion 37 may be of a small torque value which is regulated by the arbitrary torque characteristic TSR (θ) and is smaller than the value of the necessary torque TN to be regulated by the necessary torque characteristic TS (θ). This makes it possible to assist the manual curving operation of the operator.

Although there is illustrated here the example in which the arbitrary torque characteristic TSR (θ) regulates the linear relationship that the torque increase ratio is constant over the entire area of the curving angle θ, the relationship may not always be linear. That is, it is also possible to employ a non-linear arbitrary torque characteristic TSR (θ) depending on the contents of the operation of the operator or the like.

Also, the difference torque (difference force) ΔT, which is obtained when the arbitrary torque Ti based on the arbitrary torque characteristic TSR (θ) is subtracted from the necessary torque TN based on the necessary torque characteristic TS (θ), is generated from the drive motor 101 as a curving assisting force. However, this is not always limitative. For example, a difference torque characteristic expressing the difference torque ΔT may be stored instead of the arbitrary torque characteristic TSR (θ) and the difference torque ΔT may be obtained using the difference torque characteristic. In this case as well, there can be provided a similar effect. Also, in this case, there is eliminated the need to calculate the difference torques one by one, thereby being able to enhance the response efficiency of the control.

The control portion 77, in order to carry out the above control, previously stores the respective pieces of information about the necessary torque characteristic TS (θ) and arbitrary torque characteristic TSR (θ) in the endoscope main body side storage portion 75 (see FIG. 1), operates the curving amount of the curving portion 33 according to an output signal from the encoder 109, while referring to the respective pieces of information at a given timing, obtains an operation assisting force to be generated, and outputs a drive signal to the motor drive circuit 107. And, the motor drive circuit 107, according to the drive signal input therein, applies to the drive motor 101 a motor drive electric power for generating an operation assisting force corresponding to the amount of the above-mentioned difference torque ΔT. Here, as the above-mentioned information, information about a difference torque between the respective torque characteristics, that is, TS (θ)−TSR (θ) may also be previously stored and this difference torque may be referred to. In this case, the operation burden of the control portion 77 can be reduced.

Here, the torque to be applied to the connecting shaft 44 when the endoscope apparatus is in actual use balances specifically in the following manner.

That is, in the case of the torque that acts on the connecting shaft 44 in the curving operation, where an operation torque caused by an operation force to be applied by the operator to the curving operation portion 37 for curving the curving portion 33 is expressed by TH, a drive torque caused by a drive force to be generated by the drive motor 101 is expressed by TM, a necessary torque or an operation force preset value regulated by the necessary torque characteristic TS (θ) and necessary to curve the curving portion 33 to a curving angle θ is expressed by TS, and a torque caused by a reaction force given to the curving portion 33 from a subject when the leading end side of the endoscope insertion portion such as the endoscope leading end portion 35 is contacted with the inner wall surface of the sample due to the curving operation is expressed by TB, the relationships of an equation (1) hold.

$$TH+TM=TS+TB \quad (1)$$

Here, as described above, in the case that the drive torque TM is defined as a difference (TM=TS−TSR) between the necessary torque TS and an arbitrary torque TSR according to a previously stored arbitrary torque characteristic TSR (θ) and the control portion outputs a drive signal to the motor drive circuit 107, the operation torque TH can be obtained as the relationships of an equation (2).

$$TH+TS-TSR=TS+TB$$

$$TH=TSR+TB \quad (2)$$

That is, the operation torque TH caused by the operation force applied to the curving operation portion 37 in the curving operation is the sum of the arbitrary torque TSR and the torque TB caused by the reaction force given from the subject.

Therefore, in the case that the reaction force from the subject acts onto the endoscope leading end portion 35, between the operation torque TH and arbitrary torque TSR, there is produced a difference equivalent to the amount of the reaction force, thereby allowing the operator to recognize that the reaction force has been produced.

As has been described heretofore, according to the endoscope apparatus having the present structure, regardless of the bending rigidity depending on the material and structure of the endoscope insertion portion 23, the characteristic of the operation torque can be matched to the characteristic of the arbitrary torque characteristic TSR (θ) that is set arbitrarily, and thus the curving operation of the curving portion 33 can be set for such an operation efficiency as can meet the taste of the operator.

Further, since the arbitrary torque characteristic TSR (θ) is set for a linear characteristic according to which the operation torque and the amount of curving are directly proportional to each other, there can be provided a more natural operation feeling. In other words, although the characteristic of the necessary torque characteristic TS (θ) is a non-linear characteristic according to which, as the curving amount increases, a force necessary for curving increases with accelerating speed, according to the present endoscope apparatus, it is possible to correct such an unnatural operation feeling as is caused by the necessary torque characteristic TS (θ).

Also, in the case of information about the necessary torque characteristic TS (θ) and arbitrary torque characteristic TSR (θ), several kinds of information about such torque characteristics can be previously stored in the endoscope main body side storage portion 75 (see FIG. 1), that is, such several kinds of information can be contained as the candidates that can be selected. In this case, according to an input instruction given from an input portion 123 which is connected to the control portion 77 of the signal processing unit 13 and serves as characteristic selecting means, a desired torque characteristic may be selected arbitrarily.

For example, multiple pieces of information respectively about the candidates of the necessary torque characteristic TS (θ) and arbitrary torque characteristic TSR (θ) previously stored in a signal processing unit side storage portion 111 and endoscope main body side storage portion 75 are listed and displayed on the monitor 17, and the operator may select a desired torque characteristic from them using a mouse, a keyboard or the like. Also, there may also be employed a structure in which a desired torque characteristic can be selected according to a simple switch change-over operation. Here, the disposition of the input portion 123 in the signal processing unit 13 is not limitative, but the input portion 123 may also be disposed in the main body operation portion 21 of the endoscope main body 11 or the like, or the input portion 123 may also be disposed at any position, provided that it allows the select information can be communicated from the input portion 123 to the control portion 77.

In addition, there may also be provided a function which, at the time when the endoscope main body 11 is connected to the signal processing unit 13, automatically selects a desired torque characteristic from the candidates of the arbitrary torque characteristic TSR (θ). In this case, this function can be realized in the following manner: that is, the torque characteristics to be selected automatically are previously specified using a mouse, a keyboard or the like, and the contents of such specification are stored in the storage portion 111 or the like.

Thus, since multiple kinds of arbitrary torque characteristics TSR (θ) are previously prepared, for example, in the case that multiple operators use the same endoscope main body 11, the respective operators can simply set such operation efficiency as can meet their tastes. Also, according to the diagnosis and cure manipulation contents that are carried out using the endoscope apparatus, a desired torque characteristic can be set selectively, thereby being able to obtain the optimum operation efficiency.

Also, since multiple kinds of necessary torque characteristic TS (θ) are previously prepared, in the case that the manipulation contents are changed sequentially, for example, in the case that, after execution of a diagnosis using an endoscope apparatus, a cure is executed successively, multiple pieces or different kinds of endoscope apparatuses are handled sequentially. Even in this case as well, since there are previously prepared the multiple kinds of necessary torque characteristics TS (θ), the relationship between the operation force and curving amount can be always kept constant regardless of the kinds or individual differences of the respective endoscope apparatuses. This can prevent the respective endoscope apparatuses from providing different operation feeling to the operator, whereby the operator can carry out stable manipulations.

Also, the operators of an endoscope apparatus may differ in the size of hands or in arm strength from each other. Thus, even in the case that the operation force of the endoscope is excessively great for one operator and thus it causes the operator to be tired easily, such operation force may be too light for the other operator to execute a delicate operation without difficulty. However, according to the above structure of the endoscope system, both of the operators can carry out the curving operations of the endoscope apparatus with the operation forces that can satisfy both of them.

Also, even in the case of the same operator, there may be a case in which the optimum operation efficiency differs depending on the object of use of the endoscope apparatus. For example, in the case that the endoscope apparatus is used for screening, since the curving portion 33 is greatly moved repeatedly, preferably, an operation force to be applied to the curving operation portion 37 may be light for relief of the fatigue of the operator. On the other hand, in the case that the endoscope apparatus is used for a cure, since the leading end portion of the endoscope apparatus must be positioned delicately, there is necessary a proper operation feeling (operation torque). Even in the case that an arbitrary torque differs in this manner depending on the manipulation contents of the diagnosis and cure to be carried out using the endoscope apparatus, the optimum operation efficiency can be easily provided all the time.

The above-mentioned respective pieces of information about the arbitrary torque characteristic TSR (θ) and necessary torque characteristic TS (θ) may be stored collectively in one storage portion, or they may be stored separately in their individual storage portions.

For example, in the case that the information about necessary torque characteristic TS (θ) is stored in the endoscope main body side storage portion 75 of the endoscope main body 11, since the necessary torque characteristic TS (θ) inherent to the endoscope main body is stored in the endoscope main body itself, it is possible to omit the setting of the necessary torque characteristic TS (θ) that is matched to an endoscope to be used. Further, in the case that the information about the arbitrary torque characteristic TSR (θ) is stored in the signal process unit side storage portion 111 of the signal process unit 13, the management of information about a large number of curving characteristics corresponding to various kinds of situations can be unified. Thus, when compared with a case in which such information is stored in individual endoscope apparatus, the management of information can be facilitated.

Also, there may also be employed a structure in which information about the arbitrary torque characteristic TSR (θ) and information about the necessary torque characteristic TS (θ), together with the individual identification information about the endoscope main body 11 (for example, the individual information about the endoscope main body 11 such as the model and ID thereof), are stored in the storage portion of an external electronic equipment which is connected to the control portion 77 in such a manner that communication is possible between them.

As the external electronic equipment, there can be used the server 19 connected to a network to which the control portion 77 is connected through an interface 113, or a storage device (not shown).

In the case that at least a portion of information about the curving characteristics is stored in the external electronic equipment connected to the endoscope apparatus, the structure of the endoscope apparatus can be simplified. Also, through communication with the external electronic equipment, there can be taken out necessary information. This can enhance the convenience of the endoscope apparatus without complicating the state of use thereof Also, in the case that the information about the curving characteristics is stored in equipment, which is connected to a network, such as the server 19, as far as the equipment can be connected to the network, information about the curving characteristic meeting the requirement of the operator can be taken out through communication. This can spread the range of use of the endoscope main body 11 and thus enhance the convenience of the endoscope apparatus.

Next, description will be given below of a modification of the above-mentioned endoscope main body 11.

Here, it is assumed that, in the diagnosis and cure using the endoscope main body 11, the leading end portion 35 of the endoscope insertion portion 23 is held in a state where it is inclined by a given angle from the straight state thereof and, in this inclined state, a specific portion of a subject is observed. In this case, the endoscope leading end portion 35 is controlled in such a manner that the endoscope leading end portion 35 is inclined about a position where it is inclined. In other words, a state, in which the curving portion 33 is curved by a given angle, is re-set as a neutral point, and the curving portion 33 is curved about this neutral point. Firstly, description will be given of the control that re-sets this neutral point.

In the case that the curving portion 33 is curved, it generates a reaction force (an elastic restoring force) which is going to return the curving portion 33 to its straight state due to its own elasticity. In order to maintain the curving portion 33 in a state where it is curved by a given angle against the restoring force, there is generated in the drive motor 101 a torque which is equivalent in size to an operation force applied to the curving operation portion 37, whereby the curved state of the curving portion 33 can be maintained.

Also, in the case that the curving operation portion 37 is operated or rotated further from the curved state of the curving portion 33 maintained by the drive motor 101, the curving portion 33 can be operated or curved about the maintained curved state thereof by an amount corresponding to the direction and force of such rotation operation.

Owing to this, as conceptually shown in FIG. 6A, the neutral point of the curving portion 33 normally held in a straight state can be re-set in a state where it is curved by an angle θc as shown in FIG. 6B.

Also, the relationship between a curving angle θ having the neutral point of the normal straight state as its center and a torque T necessary for curving the curving portion 33 (a torque depending on the bending rigidity of the curving portion 33), conceptually, provides such a characteristic as shown in FIG. 7A. That is, a curving angle θ when an operation torque is not loaded is zero degrees. On the other hand, the drive motor 101, which is used to set the curving angle θc of the curving portion 33 as a neutral point, as shown in FIG. 7B, generates a bias assisting force of a constant level regardless of the curving angle θ.

Therefore, for example, when the curving angle θ is changed by an angle α from a state where the curving angle θ is +θ, in such a normal case as shown in FIG. 6A where a neutral point is not re-set, as shown in FIG. 7A, there is necessary an operation torque T0 corresponding to an increase in a curving angle (θ+α). Also, in the case that such a neutral point as shown in FIG. 6B is re-set, as shown in FIG. 7C, there is necessary only an operation torque Tc corresponding to an increase in the curving angle α. Accordingly, in the case that a neutral point is reset, there can be reduced an operation force to be applied to the curving operation portion 37 when carrying out a curving operation in the vicinity of the neutral point, thereby being able to lighten the burden of the operator. Especially, since the larger the curving angle is, the more necessary the operation force is, when increasing the curving amount, the operation force can be reduced greatly.

In the present modification, in the case that the neutral point of the curving portion 33 is re-set in the above-mentioned manner, even when the necessary torque characteristic TS (θ) has a non-linear characteristic, the curving portion 33 can be operated or curved on the assumption that such necessary torque characteristic is a torque characteristic according to which the curving angle and operation torque are in direct proportion to each other.

Figure 8:
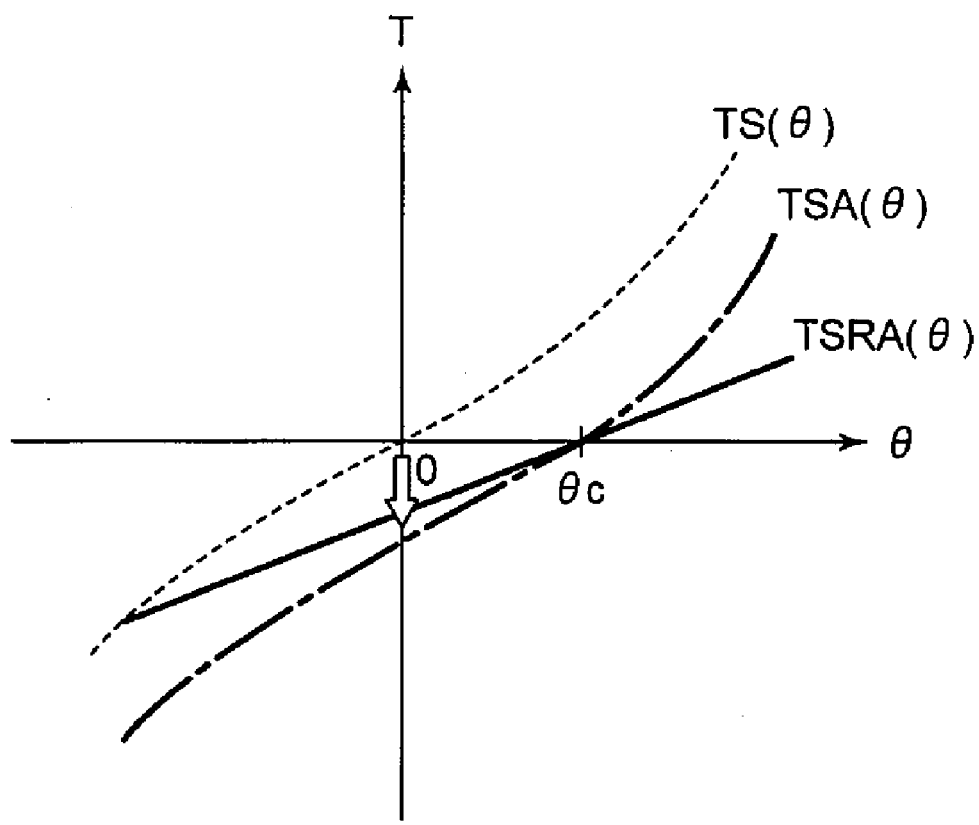
FIG. 8 is a graphical representation of a torque characteristic in the case that the neutral point of the curving portion is re-set.

FIG. 8 shows a torque characteristic when the neutral point of the curving portion is re-set. In FIG. 8, a necessary torque characteristic TS (θ) shown by a dotted line when a neutral point is not re-set is a non-linear torque characteristic according to which an increase in the necessary torque varies at every curving angles with respect to an increase in the curving amount of the curving portion 33. According to the necessary torque characteristic TS (θ), in the case that the neutral point is re-set, there is offset a torque which is necessary to maintain the neutral point to be re-set. That is, the necessary torque characteristic TS (θ) is shifted downward in FIG. 8 to thereby provide a corrected torque characteristic TSA (θ) which is shown by a one-dot chained line in FIG. 8. The corrected torque characteristic TSA (θ) is a torque characteristic according to which, when an operation torque is zero in cooperation with the drive motor 101, the curving angle θ provides the curving angle θc of the neutral point.

However, the corrected torque characteristic TSA (θ) is a non-linear torque characteristic. Therefore, in the case that the curving portion 33 is operated or curved according to the corrected torque characteristic TSA (θ), a torque necessary in a direction to increase the curving amount of the curving portion 33 from the curving angle θc of the neutral point is different from a torque necessary in a direction to decrease such curving amount, thereby causing the operator to feel discomfort when the operator drives the curving operation portion 37 to curve the curving portion 33. In view of this, in the endoscope apparatus according to the present modification, an arbitrary toque characteristic TSRA (θ) is defined as a torque characteristic according to which, for the curving angle θc, the operation torque is zero and an increase in the operation torque with respect to an increase in the curving amount is constant regardless of the curving angle. Owing to this, while the re-set neutral point is used as the center thereof, increases in the necessary torque in the increasing and decreasing directions of the curving angle of the curving portion 33 can be made substantially equal to each other.

Also, even in the case that the arbitrary toque characteristic TSRA (θ) is not defined as the above-mentioned linear torque characteristic but is defined as a non-linear torque characteristic according to which an increase in the operation torque varies with respect to an increase in the curving amount of the curving portion 33, according to the following technique, increases in the necessary torque in the increasing and decreasing directions of the curving angle of the curving portion 33 can be made equal to each other.

Figure 9:
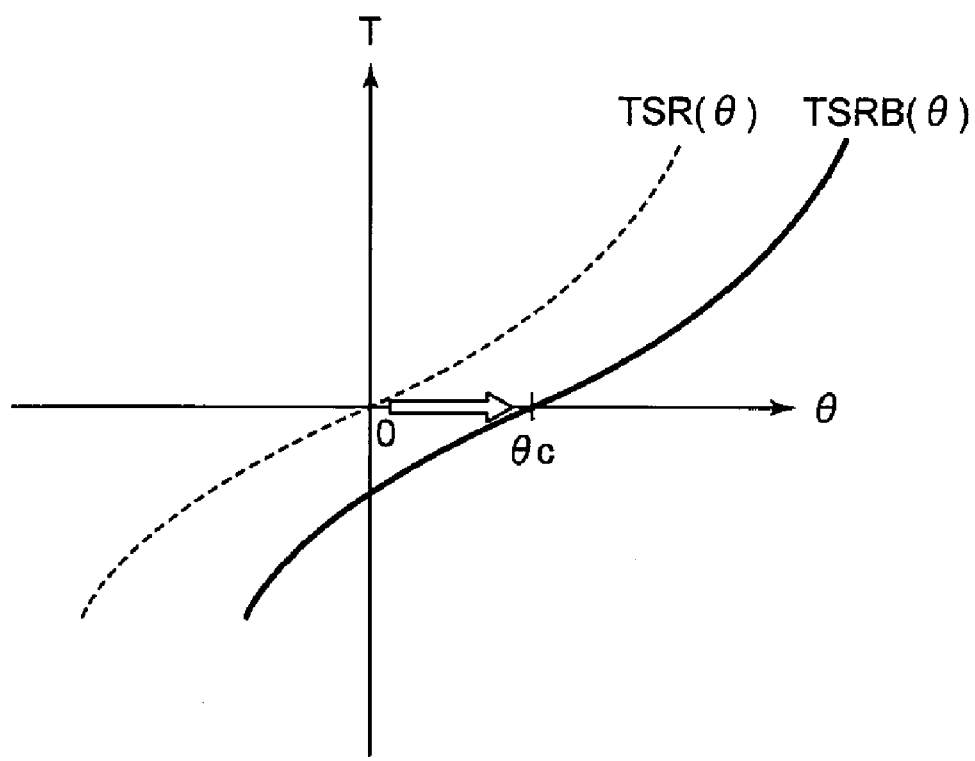
FIG. 9 is a graphical representation of an arbitrary torque characteristic TSRB (θ) obtained in the case that a non-linear arbitrary torque characteristic TSR (θ) is corrected when the neutral point of the curving portion is re-set.

In FIG. 9, there is shown an arbitrary toque characteristic TSRB (θ) which is a corrected version of a non-linear arbitrary torque characteristic TSR (θ) when the neutral point of the curving portion is re-set. As shown by a dotted line in FIG. 9, in the case that an arbitrary torque characteristic TSR (θ) with the neutral point not re-set is defined as a non-linear torque characteristic, the curving angle θc of the curving portion 33 at the re-set neutral point is detected using the above-mentioned encoder 109, and the arbitrary torque characteristic TSR (θ) is shifted (in the right direction in FIG. 9) by an amount equivalent to the curving angle θc. The thus obtained torque characteristic is defined as an arbitrary toque characteristic TSRB (θ) when the neutral point is re-set.

In other words, even for a non-linear torque characteristic, in the case that a torque characteristic at curving angles before and behind the neutral point not re-set is used at curving angles before and behind the neutral point after re-set, in the increasing and decreasing directions of the curving angle of the curving portion 33, increases in the necessary torque can be made equal to each other.

That is, an arbitrary toque characteristic TSRB (θ) when the neutral point is re-set can be obtained from an arbitrary torque characteristic TSR (θ) with the neutral point not re-set according to the following equation (3).

$$TSRB(\theta) = TSR(\theta - \theta c) \quad (3)$$

In this equation, a curving angle θc is a curving angle at the time when the neutral point is re-set.

And, a drive torque TM, which is caused by a drive force generated by the drive motor 101 and is applied to the connecting shaft 44 in the curving operation, similarly to the above-mentioned case, can be obtained as a difference between a necessary torque TS necessary for curving the curving portion according to the necessary torque characteristic TS (θ) and a torque TSRB according to the corrected arbitrary torque characteristic TSRB (θ).

$$TM = TS - TSRB \quad (4)$$

Owing to this, with the re-set neutral point as the center thereof, increases in the operation torque in the increasing and decreasing directions of the curving amount of the curving portion 33 can be made substantially equal to each other.

Therefore, according to the structure of the present modification, in the case that the neutral point of the curving portion 33 is re-set, by changing the arbitrary torque characteristic like TSRA (θ) and TSRB (θ) according to the curving angle θc of the re-set neutral point, the operator can be prevented from feeling discomfort in the curving operation.

Here, the respective structures described heretofore with reference to the above-mentioned endoscope apparatus and its modification may be employed independently or in combination.

Next, description will be given below of an endoscope apparatus structured such that, in the curving operation of the curving portion 33, it detects an operation torque caused by an operation force to be applied to the curving operation portion and, according to the relationship between the operation torque and the curving amount of the curving portion 33, can control a reaction force given to the leading end portion of the endoscope from a subject.

Figure 10:
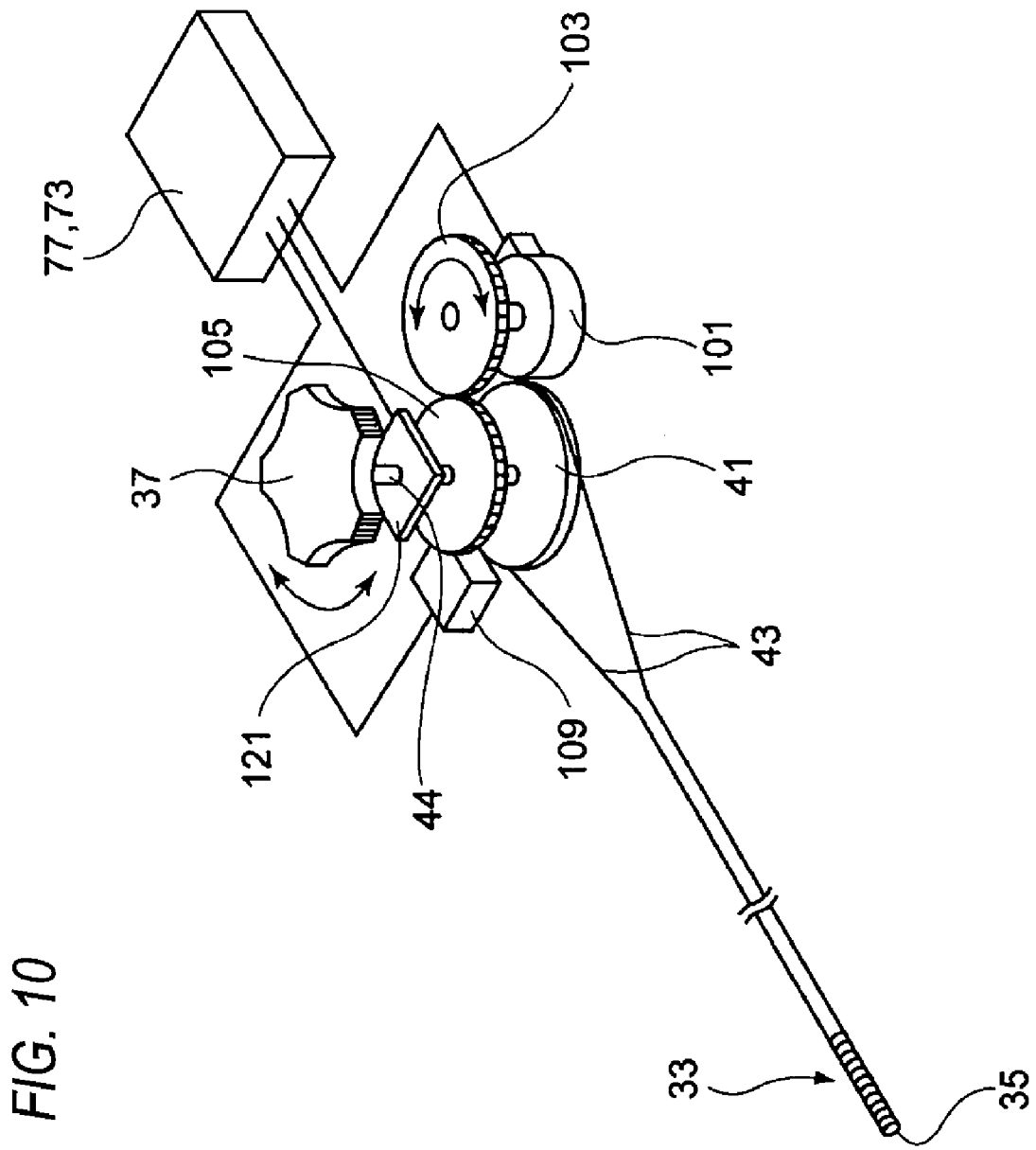
FIG. 10 is a typical structure view of a structure in which an operation torque detecting function is added to the drive mechanism for curving the curving portion.

FIG. 10 is a typical view of a structure of a drive mechanism for curving the curving portion to which there is added a function to detect an operation torque. This drive mechanism is similar in structure to the drive mechanism shown in FIG. 4, except that a torque sensor 121 serving as an operation force detecting device is provided on the curving operation portion 37 of the drive mechanism. Therefore, the same composing parts of the present drive mechanism are given the same designations as those shown in FIG. 4 and thus the description thereof is omitted or simplified here.

On the connecting shaft 44, there is provided a torque sensor 121 serving as an operation force detecting device. This torque sensor 121 detects a rotation torque to be applied to the connecting shaft 44 due to the rotation operation of the curving operation portion 37, and outputs as an operation torque to the control portion 77. As the torque sensor 121 which is disposed on the connecting shaft 44, there can be used various kinds of known torque sensors such as a torque sensor using a magnetic strain gauge and a torque sensor of a magnetic strain type. Here, to detect this operation torque, there can also be used various types of detecting devices other than the torque sensors.

Also, in an endoscope main body including a curving drive portion having the above-mentioned torque sensor 121, similar to the previously described endoscope main body 11, there is obtained the curving angle of the curving portion 33 according to a detection signal given from the encoder 109 and, with reference to information about an arbitrary torque characteristic, there is obtained a drive torque produced by the drive motor 101 and corresponding to the thus obtained curving angle. And, the control portion 77 outputs to the motor drive circuit 107 a drive signal for generating the thus obtained drive torque, whereby the drive motor 101 is driven to generate a curving assisting force due to which the curving portion 33 can be curved to a desired curving angle. Owing to this, an operation torque caused by an operation force to be applied to the curving operation portion 37 can be matched to an arbitrary torque characteristic.

And, using the torque sensor 121, there is detected an operation torque caused by an operation force applied to the curving operation portion 37 in order to curve the curving portion 33. Then, there is found a difference between the thus detected operation torque and a torque value provided by a previously set arbitrary torque characteristic. And, the difference is defined as a reaction force given to the endoscope leading end portion 35 from a subject because the endoscope leading end portion 35 and the subject are contacted with each other, and, by controlling the drive motor 101, such reaction force is transmitted to the operator in such a manner that it is reduced or emphasized.

In other words, in the case that there is generated resistance in the curving operation, for example, the endoscope leading end portion 35 receives a reaction force from the subject, even when the curving operation portion 37 is operated to thereby apply an operation torque to the curving portion 33, the curving portion 33 is prevented from reaching a curving angle in the arbitrary torque characteristic corresponding to the operation torque applied. In view of this, in order that, when resistance is generated in the curving operation of the curving portion 33, the operator can easily recognize the generation of this resistance or can reduce the operation force, the amount of generation of a drive torque in the curving operation is changed. That is, in the case that the generated resistance is transmitted to the operator in an emphasized manner, there is reduced a drive torque which is calculated according to the arbitrary torque characteristic and is to be generated by the drive motor 101. In this case, since the operation force necessary for the curving operation increases, the operator can easily feel that a reaction force is given from the subject.

Also, in the case that the generated resistance is transmitted to the operator in a reduced manner, a portion or all of a torque loss caused by the resistance is superimposed on the drive torque according to the arbitrary torque characteristic. In this case, it is possible to reduce the operation force of the operator who operates the curving operation portion against the reaction force given from the subject.

In this manner, there can be changed freely the degree to which the operator can recognize the reaction force given to the endoscope leading end portion 35, and the operation force of the operator.

Here, description will be given specifically of the drive torque that is generated by the drive motor 101.

That is, in the case of the torque that acts on the connecting shaft 44 in the curving operation, where an operation torque caused by an operation force to be applied to the curving operation portion 37 is expressed by TH, a drive torque caused by the drive force of the drive motor 101 is expressed by TM, a necessary torque regulated by the necessary torque characteristic and necessary for curing the curving portion 33 is expressed by TS, and a torque caused by a reaction force given to the curving portion 33 from a subject is expressed by TB, as described above, the relationships of the following equation (5) hold.

$$TH+TM=TS+TB \quad (5)$$

The control portion 77, using the encoder 109 and torque sensor 121 respectively shown in FIG. 10, detects momentarily changing curving angles θ and operation torques TH and, according to the detected values thereof, finds the drive torque TM to be generated by the drive motor 101 from the following equation (6).

$$TM=(TS-TSR)+k(TH-TSR) \quad (6)$$

In this equation, k is a constant parameter which decides the amount of operation assisting torques.

The thus obtained drive torque TM is generated by the drive motor 101. In this case, the balance of a force around the connecting shaft 44 is expressed by the following equation (7), and also the operation torque TH can be expressed by the following equation (8).

$$TH+(TS-TSR)+k(TH-TSR)=TS+TB \quad (7)$$

$$TH=TSR+\{1/(1+k)\}TB \quad (8)$$

As shown in the equation (8), the operation torque TH is the sum of a torque value according to a previously stored arbitrary torque characteristic TSR (θ) and a torque which is the product of the torque TB caused by the reaction force from the subject and a constant "1/(1+k)".

That is, assuming that "1/(1+k)" is a constant less than 1, while the arbitrary torque TSR according to the arbitrary torque characteristic TSR (θ) remains as it is, the reaction force from the subject can be transmitted to the operator in such a manner that it is reduced properly. Also, assuming that "1/(1+k)" is a constant more than 1, the reaction force from the subject can be transmitted to the operator in such a manner that it is emphasized.

In other words, in the case that a reaction force from the subject is not generated (TB=0), the operation toque TH is set according to the arbitrary torque characteristic TSR (θ) that can be set arbitrarily; and, in the case that a reaction force from the subject is generated (TB>0), the operation toque TH is set in such a manner that a value, which is obtained as the product of the torque TB caused by the reaction force and a proper set value of the reduction ratio "1/(1+k)" included in the equation (8), is superimposed on the arbitrary torque TSR according to the arbitrary torque characteristic TSR (θ). Owing to this, the size of the reaction force to be transmitted to the operator can be controlled, that is, can be emphasized or reduced independently of a drive torque component which is to be matched to the arbitrary torque characteristic TSR (θ).

Here, description will be given below of a curving operation which is carried out by an endoscope apparatus having the present structure with reference to FIG. 11.

Figure 11A:
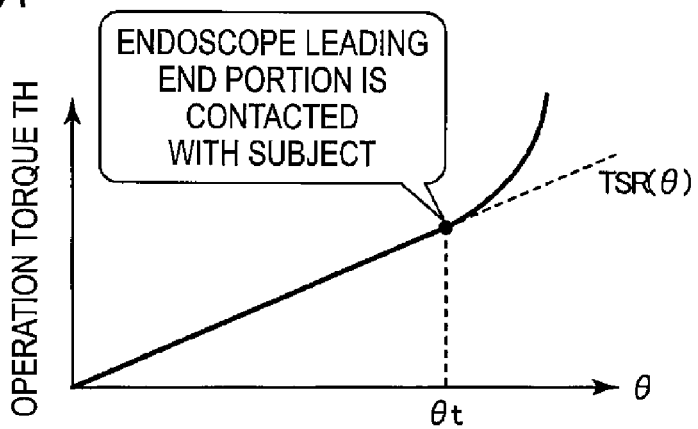
FIG. 11A is an explanatory view of the relationship of the operation torque with respect to the curving angle.
Figure 11B:
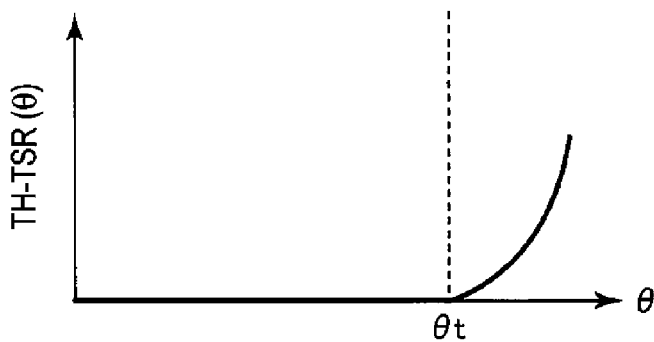
FIG. 11B is an explanatory view of the relationship of the difference between the operation torque and an arbitrary torque characteristic with respect to the curving angle.

In the case that the reaction force emphasis or reduction control is not carried out, that is, in the case that k is zero in the equation (6), as shown in FIG. 11A, as the operation torque TH increases, the curving angle θ of the curving portion 33 increases. However, at and from a curving angle θt where the leading end side of the endoscope insertion portion 23 is contacted with the subject, the curving portion 33 is hard to be curved due to the torque TB caused by the reaction force given to the curving portion 33 from the subject. In the case that the then operation force is detected using the torque sensor 121 and a difference between the thus detected operation force and a torque value regulated by the arbitrary torque characteristic TSR (θ) is found, as shown in FIG. 11B, the difference increases at and from the curving angle θt where the endoscope leading end portion is contacted with the subject.

Figure 11C:
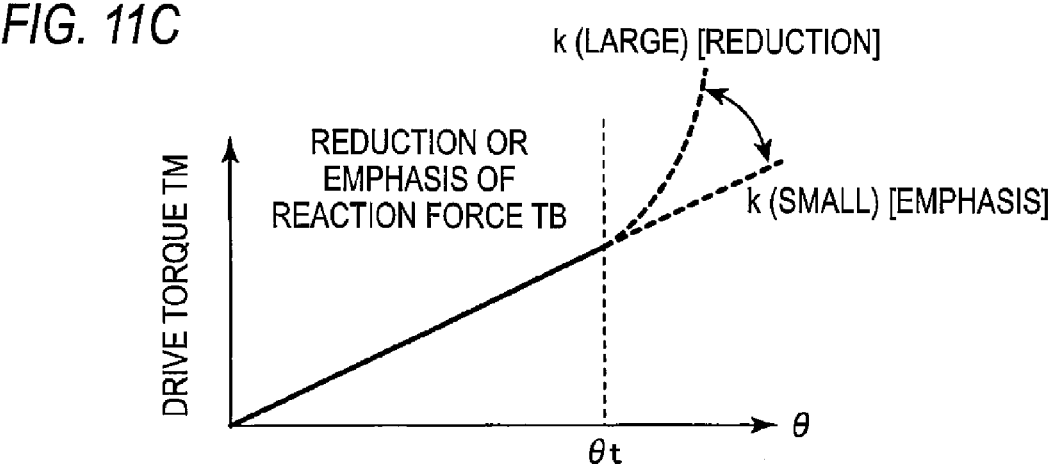
FIG. 11C is an explanatory view of the relationship of the drive torque with respect to the curving angle.

Thus, as shown in FIG. 11C, the drive torque to be generated by the drive motor 101 at and from the curving angle θt is increased or decreased depending on the setting of the constant parameter k. Specifically, in the case that k is increased, the term k (TH−TSR) of the equation (6) increases and the drive torque TM reduces variations in the operation torque TH caused by the torque TB. In the case that k is decreased, reversely, variations in the operation torque TH caused by the torque TB depending on the reaction force are emphasized.

Therefore, in the case that the reaction force from the subject acts on the curving portion 33, the operation torque TH is shifted from the arbitrary torque characteristic TSR (θ) by an amount equivalent to the reaction force, thereby allowing the operator to recognize that the reaction force has been generated. And, the size of the shift of the operation torque TH from the arbitrary torque characteristic TSR (θ) to be transmitted to the operator can be set arbitrarily by increasing or decreasing the constant parameter k.

Here, in the above-mentioned structure example, by selecting a specific curving characteristic, an assisting drive force is decided and, according to the decision result, the operation torque is decided. However, this is not limitative but, for example, the operation torque may be calculated according to a specific curving characteristic and, according to the calculation result, an assisting drive torque may be decided. Also, in the above structure example, there is illustrated a case in which an endoscope apparatus is an electronic scope for picking up the image of an observation portion using an imaging element such as a CCD image sensor. However, this is not limitative but, for example, an endoscope apparatus may also be a fiber scope which includes an observation lens, an observation window and the like in the leading end portion thereof and observes an observation portion directly.

As has been described above heretofore, the invention is not limited to the above embodiment but the invention connotes that, according to the description of the specification and well-known technology, persons skilled in the art can change and apply the embodiment. Such changes and applications naturally fall under the scope of the appended patent claims of the invention.

As described above, the present specification discloses the following articles.

(1) An endoscope apparatus includes an endoscope main body, a curving amount detecting unit, an assisting drive unit, a storage unit and a control unit. The endoscope main body includes (i) an endoscope insertion portion having a curving portion on the leading end side thereof, (ii) a curving operation portion operating or curving the curving portion, and (iii) a curving drive portion driving or curving the curving portion according to an operation force applied to the curving operation portion. The curving amount detecting unit detects curving amount of the curving portion. The assisting drive unit generates a drive force for assisting a curving drive operation carried out by the curving drive portion. The storage unit stores multiple pieces of curving information respectively regulated at every curving angles corresponding to curving amounts of the curving portion. The control unit controls the assisting drive unit to generate the drive force according to the curving amount detected by the curving amount detecting unit. The control unit controls the assisting drive unit to generate the drive force using the curving information stored in the storage unit.

(2) In the endoscope apparatus of (1), the curving information includes at least one of a first curving characteristic according to which the operation force necessary for the curving operation of the curving portion is regulated at each curving angle, a second curving characteristic according to which the operation force defined arbitrarily is regulated at each curving angle of the curving portion, and a third curving characteristic according to which a difference between the first and second curving characteristics is regulated at each curving angle.

(3) In the endoscope apparatus of (2), the control unit controls the assisting drive unit to generate the drive force calculated from a difference between the first and second curving characteristics.

According to the present endoscope apparatus, when curving the curving portion through the curving operation from the operation portion, the curving amount is detected using curving amount detecting means, a necessary operation force corresponding to the thus detected curving amount is obtained according to the first curving characteristic, and an arbitrary operation force is obtained according to the second curving characteristic. And, since a difference force between the necessary operation force and arbitrary operation force is generated by assisting drive means, correspondingly to an operation force applied to the operation portion, the curving portion is curved according to the second curving characteristic. In other words, regardless of the bending rigidity of the curving portion, the curving operation can be carried out according to an arbitrary characteristic and the curving operation of the curving portion can be set for an operation characteristic which meets the taste of the operator.

(4) In the endoscope apparatus of (2), the control unit controls the assisting drive unit to generate the drive force according to the third curving characteristic.

According to the present endoscope apparatus, due to use of the third curving characteristic, there is eliminated the need to calculate and obtain differences between the first and second curving characteristics one by one, thereby being able to enhance the response efficiency of the control of the control means.

(5) In the endoscope apparatus of any one of (2) to (4), the storage unit stores therein multiple pieces of mutually different candidates of the second or third curving characteristic.

(6) In the endoscope apparatus of (5), further includes a curving characteristic specifying unit. The curving characteristic specifying unit selects a specific curving characteristic from the multiple candidates of the second curving characteristic or the multiple candidates of the third curving characteristic respectively stored in the storage unit. The control unit calculates the drive force generated from the assisting drive unit using the curving characteristic selected by the curving characteristic specifying unit.

According to the present endoscope apparatus, since there are previously prepared multiple candidates of arbitrary curving characteristics and a desired arbitrary curving characteristic is selected from them using characteristic selecting means, the endoscope apparatus can be always operated and curved with the optimum operation efficiency regardless of differences between the tastes of operators, individual differences between endoscope apparatuses, the contents of diagnosis or cure manipulations, and the like.

(7) In the endoscope apparatus of (5), according to an endoscope main body to be connected to the endoscope apparatus, a curving characteristic is automatically selected from the multiple candidates of the curving characteristics. The selected curving characteristic is used to calculate the drive force which is generated from the assisting drive unit.

According to the present endoscope apparatus, when the endoscope main body is connected to the endoscope apparatus, there can be calculated a drive force according to a curving characteristic corresponding to the connected endoscope main body.

(8) In the endoscope apparatus of (5), further includes a curving characteristic specifying unit. The curving characteristic specifying unit selects a specific curving characteristic from the multiple candidates of the second curving characteristic or the multiple candidates of the third curving characteristic respectively stored in the storage unit. The operation force is calculated from the curving characteristic selected by the curving characteristic specifying unit.

According to the present endoscope apparatus, there can be calculated an operation force according to the selected curving characteristic and a drive force is decided such that it is equal to the calculated operation force.

(9) In the endoscope apparatus of any one of (1) to (8), the control unit superimposes a bias assisting force of a given constant level on a difference force generated by the assisting drive unit. The curving portion re-sets its given-amount-curved state at the neutral point of the curving drive.

According to the present endoscope apparatus, by superimposing the bias assisting force on the difference force using the assisting drive means, the neutral point of the curving portion can be re-set and, with the re-set neutral point as the center thereof, the curving portion can be operated and curved with the operation efficiency that meets the desire of an operator.

(10) In the endoscope apparatus of any one of (1) to (8), further includes an operation force detecting unit. The operation force detecting unit detects the operation force to be applied to the curving operation portion. The control unit increases or decreases the drive force to be generated by the assisting drive unit correspondingly to a difference between an arbitrary operation force corresponding to the curving amount using the second or third curving characteristic and the operation force detected by the operation force detecting unit.

According to the present endoscope apparatus, in the case that there is generated a difference between an actually applied operation force and an operation force according to the arbitrary curving characteristic, by increasing or decreasing the drive force generated by the assisting drive means, the difference can be transmitted to the operator in such a manner that it is emphasized or reduced.

(11) In the endoscope apparatus of any one of (1) to (10), the storage unit stores at least a portion of information about the first, second and third curving characteristics in a storage portion provided in the endoscope main body.

According to the present endoscope apparatus, since the storage means is incorporated in the endoscope main body, the respective pieces of information about the first and second curving characteristics can be stored together in the endoscope main body, which can save the time and labor to store them through communication or the like and thus can enhance the convenience of the endoscope apparatus.

(12) An endoscope system includes an endoscope apparatus according to any one of (1) to (11) and, an external electronic equipment. The external electronic equipment is connected to the endoscope apparatus in such a manner that it is allowed to communicate with the endoscope apparatus. The storage unit stores the curving information in a storage portion provided in the external electronic equipment.

According to the present endoscope system, since the curving information is stored in the external electronic equipment connected to the endoscope apparatus, the endoscope apparatus can be simplified and the necessary information can be taken out from the external electronic equipment through communication. Owing to this, the convenience of the endoscope apparatus can be enhanced without complicating the structure of the endoscope apparatus.

(13) A method for controlling an endoscope apparatus which includes an endoscope main body and an assisting drive. The endoscope main body includes (i) an endoscope insertion portion having a curving portion on the leading end side thereof, (ii) a curving operation portion operating or curving the curving portion and (iii) a curving drive portion driving or curving the curving portion according to an operation force to be applied to the curving operation portion. The assisting drive unit generates a drive force for assisting a curving drive operation to be carried out by the curving drive portion. The endoscope controlling method includes: storing curving information regulated at each curving angle corresponding to curving amounts of the curving portion previously; detecting curving amount of the curving portion; and generating the drive force by the assisting drive unit using the curving information corresponding to the detected curving amount.

(14) In the endoscope controlling method of (13), the curving information includes at least one of a first curving characteristic according to which the operation force necessary for the curving operation of the curving portion is regulated at each curving angle, a second curving characteristic according to which the operation force defined arbitrarily is regulated at each curving angle of the curving portion, and a third curving characteristic according to which a difference between the first and second curving characteristics is regulated at each curving angle.

(15) In the endoscope controlling method of (14), the assisting drive unit generates the drive force calculated from a difference between the first and second curving characteristics.

According to the present endoscope apparatus controlling method, since the drive force is generated in the curving drive portion using the assisting drive means according to the difference force between the necessary operation force and arbitrary operation force, the curving portion can be curved according to the second curving characteristic correspondingly to the operation force applied to the operation portion. In other words, the curving portion can be operated or curved according to an arbitrary characteristic regardless of the bending rigidity of the curving portion, and thus the curving operation of the curving portion can be set for the operation efficiency that meets the need of the operator.

(16) In the endoscope controlling method of (14), the assisting drive unit generates the chive force according to the third curving characteristic.

(17) In the endoscope controlling method of (15) or (16), the curving amount of the curving portion and the operation force to be applied to the curving operation portion are detected respectively. An arbitrary operation force corresponding to the detected curving amount is obtained from the second or third curving characteristic. The drive force to be generated by the assisting drive unit is increased or decreased using a difference between the arbitrary operation force and the detected operation force.

According to the present endoscope apparatus controlling method, in the case that there is generated a difference between an operation force to be applied to the curving operation portion and an arbitrary operation force, the drive force can be increased or decreased correspondingly to the difference using the assisting drive means. Therefore, the difference between the operation force and arbitrary operation force can be transmitted to the operator in an emphasized or reduced manner.

What is claimed is:

1. An endoscope apparatus comprising:
    an endoscope main body that includes (i) an endoscope insertion portion having a curving portion on the leading end side thereof, (ii) a curving operation portion operating or curving the curving portion, and (iii) a curving drive portion driving or curving the curving portion according to an operation force applied to the curving operation portion;
    a curving amount detecting unit that detects curving amount of the curving portion;
    an assisting drive unit that generates a drive force for assisting a curving drive operation carried out by the curving drive portion;
    a storage unit that stores multiple pieces of curving information respectively regulated at every curving angle corresponding to curving amounts of the curving portion; and,
    a control unit that controls the assisting drive unit to generate the drive force according to the curving amount detected by the curving amount detecting unit,
    wherein the control unit controls the assisting drive unit to generate the drive force using the curving information stored in the storage unit, and
    wherein the curving information includes at least one of a first curving characteristic according to which the operation force necessary for the curving operation of the curving portion is regulated at each curving angle, a second curving characteristic according to which the operation force defined arbitrarily is regulated at each curving angle of the curving portion, and a third curving characteristic according to which a difference between the first and second curving characteristics is regulated at each curving angle.

2. The endoscope apparatus according to claim 1,
    wherein the control unit controls the assisting drive unit to generate the drive force calculated from a difference between the first and second curving characteristics.

3. The endoscope apparatus according to claim 1,
    wherein the control unit controls the assisting drive unit to generate the drive force according to the third curving characteristic.

4. The endoscope apparatus according to claim 1,
    wherein the storage unit stores therein multiple pieces of mutually different candidates of the second or third curving characteristic.

5. The endoscope apparatus according to claim 4, further comprising:
    a curving characteristic specifying unit that selects a specific curving characteristic from the multiple candidates of the second curving characteristic or the multiple candidates of the third curving characteristic respectively stored in the storage unit,
    wherein the control unit calculates the drive force generated from the assisting drive unit using the curving characteristic selected by the curving characteristic specifying unit.

6. The endoscope apparatus according to claim 4,
    wherein, according to an endoscope main body to be connected to the endoscope apparatus, a curving characteristic is automatically selected from the multiple candidates of the curving characteristics, and
    the selected curving characteristic is used to calculate the drive force which is generated from the assisting drive unit.

7. The endoscope apparatus according to claim 4, further comprising:
    a curving characteristic specifying unit that selects a specific curving characteristic from the multiple candidates of the second curving characteristic or the multiple candidates of the third curving characteristic respectively stored in the storage unit,
    wherein the operation force is calculated from the curving characteristic selected by the curving characteristic specifying unit.

8. The endoscope apparatus according to claim 1,
    wherein the control unit superimposes a bias assisting force of a given constant level on a difference force generated by the assisting drive unit, and
    a neutral point of the curving portion is re-set in a state where it is curved.

9. The endoscope apparatus according to claim 1, further comprising:
    an operation force detecting unit that detects the operation force to be applied to the curving operation portion,
    wherein the control unit increases or decreases the drive force to be generated by the assisting drive unit correspondingly to a difference between an arbitrary operation force corresponding to the curving amount using the second or third curving characteristic and the operation force detected by the operation force detecting unit.

10. The endoscope apparatus according to claim 1,
    wherein the storage unit stores at least a portion of information about the first, second and third curving characteristics in a storage portion provided in the endoscope main body.

11. An endoscope system comprising:
    an endoscope apparatus according to claim 1; and
    an external electronic equipment to be connected to the endoscope apparatus in such a manner that it is allowed to communicate with the endoscope apparatus,
    wherein the storage unit stores the curving information in a storage portion provided in the external electronic equipment.

12. A method for controlling an endoscope apparatus which includes an endoscope main body having (i) an endoscope insertion portion having a curving portion on the leading end side thereof, (ii) a curving operation portion operating or curving the curving portion and (iii) a curving drive portion driving or curving the curving portion according to an operation force to be applied to the curving operation portion, and an assisting drive unit generating a drive force for assisting a curving drive operation to be carried out by the curving drive portion, the endoscope controlling method comprising:

storing curving information regulated at each curving angle corresponding to curving amounts of the curving portion previously, detecting curving amount of the curving portion, and generating the drive force by the assisting drive unit using the curving information corresponding to the detected curving amount, wherein the curving information includes at least one of a first curving characteristic according to which the operation force necessary for the curving operation of the curving portion is regulated at each curving angle, a second curving characteristic according to which the operation force defined arbitrarily is regulated at each curving angle of the curving portion, and a third curving characteristic according to which a difference between the first and second curving characteristics is regulated at each curving angle.

13. The endoscope controlling method according to claim 12, wherein the assisting drive unit generates the drive force calculated from a difference between the first and second curving characteristics.

14. The endoscope controlling method according to claim 13, wherein the curving amount of the curving portion and the operation force to be applied to the curving operation portion are detected respectively, an arbitrary operation force corresponding to the detected curving amount is obtained from the second or third curving characteristic, and the drive force to be generated by the assisting drive unit is increased or decreased using a difference between the arbitrary operation force and the detected operation force.

15. The endoscope controlling method according to claim 12, wherein the assisting drive unit generates the drive force according to the third curving characteristic.

* * * * *